United States Patent [19]

Grunwald

[11] Plant 4,162

[45] Dec. 6, 1977

[54] CHRYSANTHEMUM NAMED BRONZE DOLLY

[75] Inventor: Walter Grunwald, Westbury, N.Y.

[73] Assignee: Pan-American Plant Company, West Chicago, Ill.

[21] Appl. No.: 768,054

[22] Filed: Feb. 14, 1977

[51] Int. Cl.[2] ..... A01H 5/00

[52] U.S. Cl. ..... Plt./79

[58] Field of Search ..... Plt./79

*Primary Examiner*—Robert E. Bagwill

*Attorney, Agent, or Firm*—Chas. W. Rummler

[57] ABSTRACT

A sport of the cultivar Dolly characterized by its unique medium bronze color and somewhat larger flower size, its other characteristics being similar to those of the parent variety.

2 Drawing Figures

BACKGROUND OF THE NEW PLANT

This chrysanthemum variety was discovered by me at Westbury, N.Y., in 1973 as a sport of a greenhouse cultured plant of the unpatented variety named Dolly. Its unique color and the larger size of the flower attracted my attention and in the expectation that the new plant would have commercial merit, I reproduced this sport by cuttings at Westbury, N.Y., and found, after propagation through several generations, that the distinctive characteristics of this plant hold true and appear to be firmly fixed. This new chrysanthemum variety is now being propagated for the commercial market by means of vegetative cuttings at West Chicago, Ill., and at Cortez, Fla., and its distinctive features continue to hold true.

DESCRIPTION OF THE DRAWINGS

My new chrysanthemum plant is illustrated by the accompanying photographic drawing which, in full color, shows the flowers and foliage of a fully developed greenhouse plant grown at West Chicago, Ill., and flowered in April, 1976, and by a second drawing showing typical leaves of the new plant, the colors shown on the first drawing being as nearly true as it is possible to obtain by conventional photographic procedures. The colors intended to be shown are represented by the painted swatches affixed to the photographic drawing.

DESCRIPTION OF THE NEW PLANT

The following is a detailed description of this new chrysanthemum variety based upon observations in greenhouse at West Chicago, Ill., with color designations according to The RHS Colour Chart published by The Royal Horticultural Society at London, England.

THE PLANT

Origin: Sport.
Parentage: Dolly (unpatented).
Classification: *Chrysanthemum morifolium.*
*Commercial.*—Greenhouse-cut flower type.
Form: Perennial, upright, herbaceous bush.
Height: 2 to 4 feet.
Growth: Terminal. Vigorous, sturdy and strong.
Branching: Normal, under natural conditions.
Foliage: Abundant, three to five leaves on 6 inches of main stem.

*Size of leaf.*—4 to 5½ inches long, 2⅛ to 3¼ inches wide.
*Shape of leaf.*—Lobed, with incised lobes.
*Surface aspect.*—Canescent.
*Color.*—Upper side — 147A; under side — 147B.
*Venation.*—Pinnate.
*Petioles.*—⅝ to 1 inch long.

THE BUD

Form: Almost globular.
Size: ⅜ to ½ inch in diameter.
Opening rate: Slow.
Color:
*When phyllaries divide.*—144A to 144B.
*When florets begin to unfurl.*—182B to 184B.
Phyllaries: Many involucral bracts borne on outside of the receptacle.
*Form.*—Spear shaped and upstanding.
*Surface texture.*—Pubescent.
*Color.*—Inside — 137A; outside — 137B.
Peduncle: 1¼ to 4 inches long and erect.
*Surface texture.*—Pubescent.

THE FLOWER

Response: 9 weeks the year around with photoperiod control.
Recommended flowering: April 15 to December 1 (Northern U.S.).
Natural flowering season: October 27 to November 4.
Blooms: Flower type — composite and decorative.
*Borne.*—The inflorescence is racemose, single flowers on long stems carried on a tall, strong stalk.
*Form.*—A head of many florets borne on a receptacle.
*Shape.*—Flat when bloom first opens. The outer florets reflex as bloom matures.
*Florets.*—Number — Very many. Form: Linear with obtuse apex. Firmness: Medium. Appearance: Very light shine. Color: Outer florets: upper side — 171B; under side — 164C. Inside florets: Upper side — 172B; under side — 164B.
Peduncle: 1¼ to 4 inches long; sturdy and upright.
*Color.*—147A to 147B.
Discoloration: Considerable fade as bloom ages.
Persistence: Florets hang on and dry.
Fragrance: Typical chrysanthemum.
Lasting quality:
*On plant.*—3 weeks.

*As cut flower.*—7 to 12 days.

REPRODUCTIVE ORGANS

Stamens: Arrangement — 5 syngenesious anthers.

*Filaments.*—1/16 to ⅛ inch long. Color: Light Yellow.

*Pollen.*—Color — Yellow.

Pistils: Number — One to each ray and disc floret.

*Styles.*—⅛ to 3/16 inch long.

*Stigmas.*—Color — Yellow.

*Ovaries.*—Inferior bicarpellate.

This new chrysanthemum cultivar is very similar to its parent Dolly in almost all characteristics, except flower color and size. Its uniqueness resides particularly in the medium bronze coloration of the blooms and their slightly larger size.

I claim:

1. A new variety of chrysanthemum plant, substantially as herein shown and described, characterized by the medium bronze coloration of its flowers and their somewhat larger size as compared to the parent variety; and ability to be flowered the year around with a substantially uniform 9-week response.

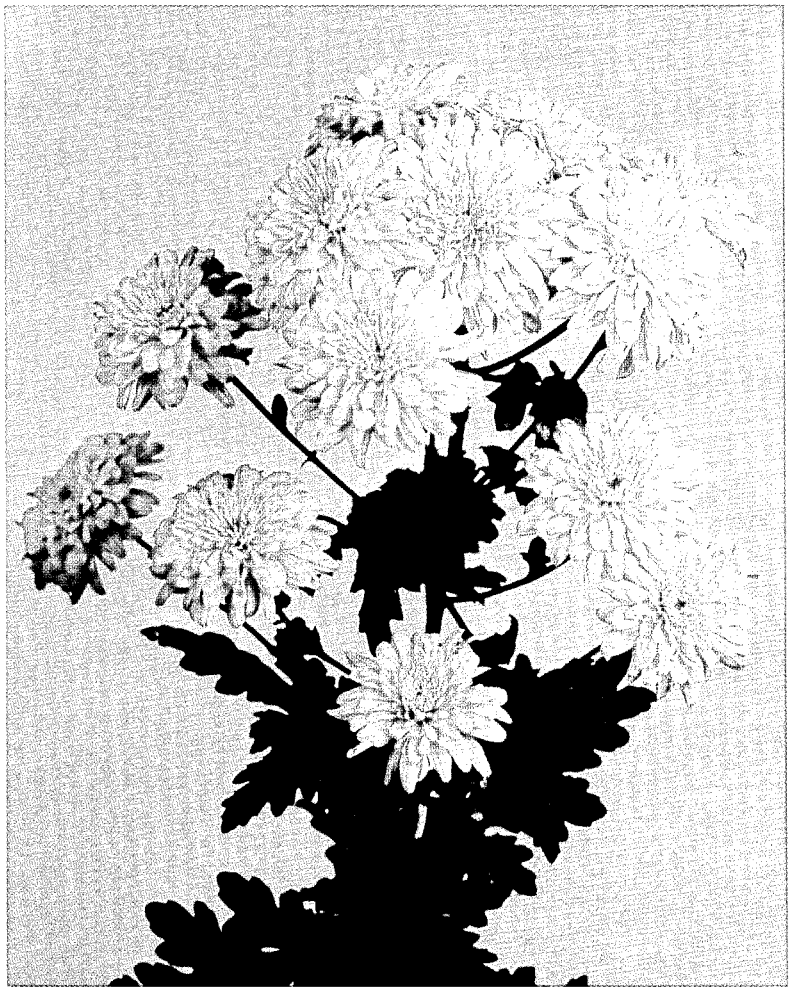
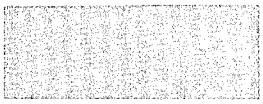
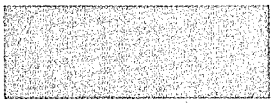

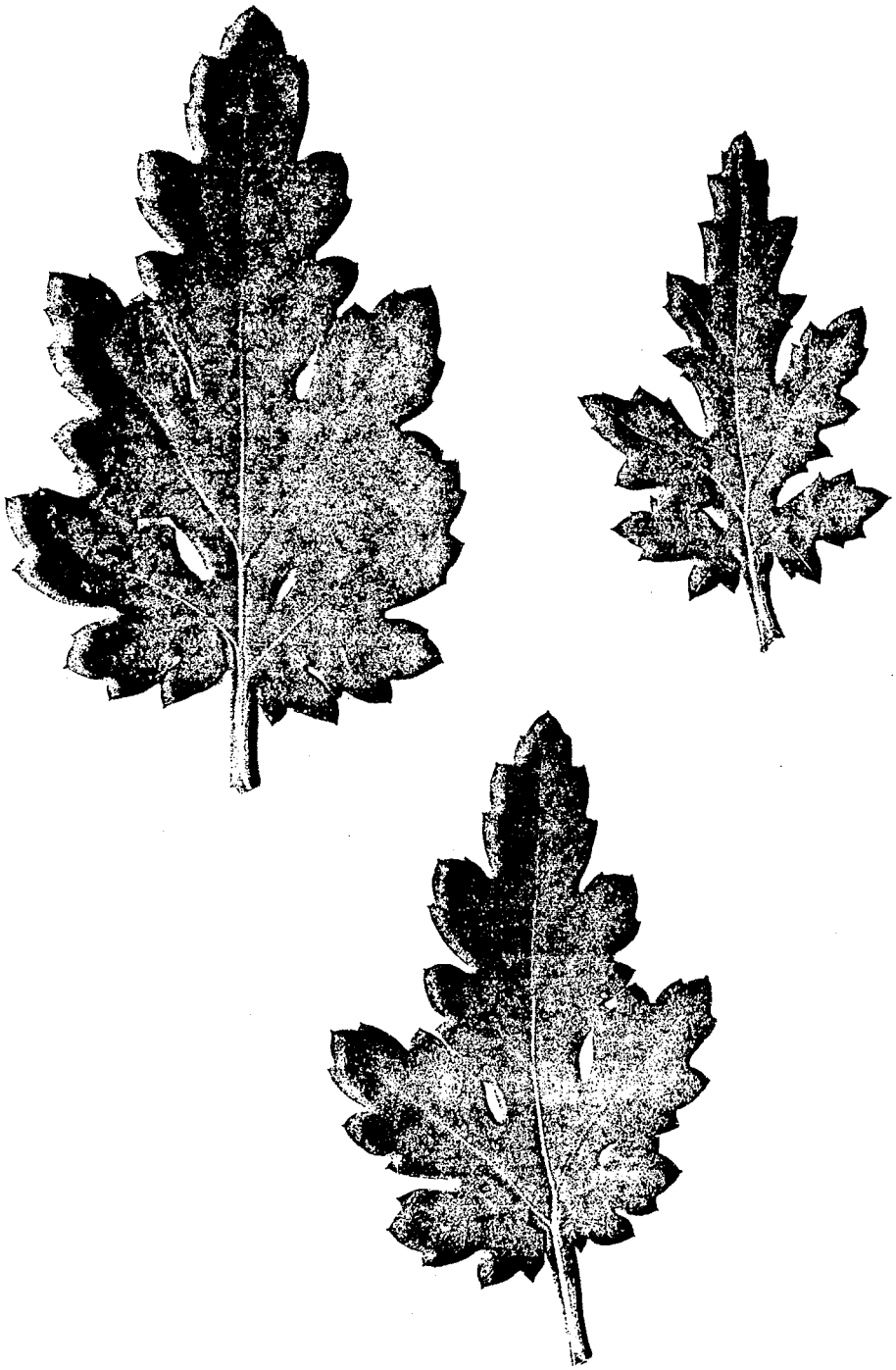

* * * * *